(12) United States Patent
Nakamura et al.

(10) Patent No.: US 7,195,789 B2
(45) Date of Patent: Mar. 27, 2007

(54) NON-FIBER EXTRACT OF PSYLLIUM WITH ANTI-TUMORIGENIC EFFECTS AND METHOD FOR IDENTIFYING THE SAME

(75) Inventors: Yasushi Nakamura, Kyoto (JP); Brad L. Upham, East Lansing, MI (US); James E. Trosko, Okemos, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 520 days.

(21) Appl. No.: 10/375,401

(22) Filed: Feb. 27, 2003

(65) Prior Publication Data
US 2003/0180400 A1    Sep. 25, 2003

Related U.S. Application Data

(60) Provisional application No. 60/362,562, filed on Mar. 7, 2002.

(51) Int. Cl.
*A61K 36/00* (2006.01)
(52) U.S. Cl. .................................................. 424/738
(58) Field of Classification Search ................. 424/738
See application file for complete search history.

(56) References Cited

U.S. PATENT DOCUMENTS 6,287,609 B1 *  9/2001  Marlett et al. ............... 424/738

OTHER PUBLICATIONS

Alabaster et al.; "Dietary fiber and the chemopreventive modelation of colon carcinogenesis," Mutation Research 350 (1996) p. 185-197.*
The Internet website http://www.wellfx.com/InfoBase/herb_Psyllium_html (2 pages).*
Gura, T. "Systems for Identifying New Drugs Are Often Faulty," Science; (1997) vol. 278, pp. 1041-1042.*
Sparreboom et al. "Herbal Remedies in the United States: Potential Adverse Interactions with Anticancer Agents," Journal of Clinical Oncology, vol. 22; No.12; Jun. 18, 2004; pp. 2489-2503. 15 pages total.*

* cited by examiner

*Primary Examiner*—Christopher Tate
*Assistant Examiner*—S. B. McCormick-Ewoldt
(74) *Attorney, Agent, or Firm*—Ian C. McLeod; Steven E. Merritt

(57) ABSTRACT

A composition comprising a non-fiber organic extract of psyllium which is anti-tumorigenic is described. The composition both restores gap junctional intercellular communication (GJIC) and inhibits anchorage independent growth of mammalian cells which have been transformed with the ras oncogene. The composition is a useful chemotherapy and chemopreventative agent. The composition was identified using a novel method for determining the anti-tumorigenic potential of a compound or composition.

11 Claims, 10 Drawing Sheets

NON-FIBER EXTRACT OF PSYLLIUM WITH ANTI-TUMORIGENIC EFFECTS AND METHOD FOR IDENTIFYING THE SAME

CROSS-REFERENCE TO RELATED APPLICATION

This application claims benefit of U.S. Provisional Application No. 60/362,562 filed Mar. 7, 2002.

STATEMENT REGARDING FEDERALLY SPONSORED RESEARCH OR DEVELOPMENT

This invention was made in the course of work supported by a National Institute of Environmental Health Sciences Grant No. PA42 ES04911. Therefore, the U.S. Government has certain rights in the invention.

Reference to a "Computer Listing Appendix submitted on a Compact Disc"

Not Applicable.

BACKGROUND OF THE INVENTION (1) Field of the Invention

The present invention relates to a non-fiber composition prepared from an organic extract of psyllium which is anti-tumorigenic. The composition both restores gap junctional intercellular communication (GJIC) and inhibits anchorage independent growth of mammalian cells which have been transformed with the ras oncogene. The composition is a useful chemotherapy and chemopreventative agent. The composition was identified using a novel method for determining the anti-tumorigenic potential of a compound or composition.

(2) Description of Related Art

Psyllium is a common source of soluble fiber derived from the husk of the plant *Plantago ovata*. Although the epidemiological evidence is not entirely consistent, dietary fiber has been linked to the prevention of cancers, particularly of the colon and breast (Greenwald et al., Eur. J. Cancer 37: 948–965 (2001); Gerber, J. Natl. Cancer Inst. 88: 857–858 (1996); Terry et al., J. Natl. Cancer Inst. 93: 525–533 (2001)). The underlying mechanisms by which dietary fiber can contribute to cancer prevention are not known. Among some of the potential mechanisms proposed for psyllium are the presence of the anticarcinogenic phytates, isoflavonoids, and protease inhibitors in psyllium fiber, and decreases in the circulation of tumor-promoting estrogens either through suppression of bacterial B-D-glucuronidase activity in the colon and cecum or direct binding of estrogens to fiber (Cohen et al., J. Natl. Cancer Inst. 88: 899–907 (1996)).

Neither the stage nor stages of the multi-step/multi-mechanism nature of the carcinogenic process is known as to where the anticarcinogenic properties of psyllium are effective. Although the effect of psyllium was most pronounced in reducing mammary adenocarcinoma, psyllium also decreased ductal carcinomas (Cohen et al., J. Natl. Cancer Inst. 88: 899–907 (1996)). Since ductal carcinomas are a morphologic continuum from an original initiating event to a fully developed carcinoma (Boone et al., Cancer Res. 52: 1651–1659 (1992)), then the clonal expansion stage of cancer development might be a target of psyllium.

One hypothesis of the tumor promotion mechanism is that the clonal expansion of an initiated cell results from a series of epigenetic events that remove this initiated cell from growth suppression via the inhibition of gap junctional intercellular communication (GJIC) and that activate mitogenic signal transduction pathways (Upham and Wagner, Toxicol. Sci. 64: 1–3 (2001); Trosko and Ruch, Front. Biosci. 3: 208–236 (1998); Rummel et al., Toxicol. Sci. 49: 232–240 (1999)). Gap junctions are channels between contiguous cells allowing the passive transfer of low molecular weight molecules, and are made up of protein subunits termed connexins (Goodenough, Annu. Rev. Biochem. 65: 475–502 (1996); Kumar and Gilula, Cell 84: 381–388 (1996)). Connexin genes have been shown to function as tumor suppressor genes (Trosko and Ruch, Front. Biosci. 3: 208–236 (1998); Yamasaki et al., Novartis. Found. Symp. 219: 241–254 (1999)). Transfection of connexin genes into neoplastic cells results in the restoration of GJIC and reversal of the transformed phenotype (de-Feijter-Rupp et al., Carcinog. 19: 747–754 (1998); Huang et al., Cancer Res. 58: 5089–5096 (1998); Hirschi et al., Cell Growth Differ. 7: 861–870 (1996); Rose et al., Carcinog. 14: 1073–1075 (1993); Mesnil et al., Cancer Res. 55: 629–639 (1995); Naus et al., Cancer Res. 52: 4208–4213 (1992)). Similarly, some anticarcinogenic compounds, such as retinoids (Mehta et al., J. Cell Biol. 108: 1053–1065 (1989); Mehta and Loewenstein, J. Cell Biol. 113: 371–379 (1991); Mehta et al., Cell 44: 187–196 (1986); Hossain et al., Carcinog. 10: 1743–1748 (1989)), carotenoids (Zhang et al., Carcinogenesis 12: 2109–2114 (1991)), caffeic acid (Na et al., Cancer Letts. 157: 31–38 (2000)) and lovastatin (Ruch et al., Mol. Carcinog. 7: 50–59 (1993)), are also known to upregulate GJIC, either by preventing the inhibition of GJIC by tumor promoters or by the restoration of GJIC in tumor cells with expressed but non-functional connexins in neoplastic cell lines that result in reversing the transformed phenotype. Green tea extract, which inhibits promotion of tumors in livers (Klaunig, Prev. Med. 21: 510–519 (1992)), also prevents the in vivo inhibition of GJIC in the liver tissues of rats treated with the tumor promoter, pentachlorophenol (Sai et al., Carcinog. 21: 1671–1676 (2000)). Published U.S. patent application Ser. No. 2001/0024664 A1 to Obukowicz et al. discloses that organic extracts prepared from edible plant materials, including psyllium, contain COX-2 inhibitory compounds which are useful for relieving pain, including pain produced by cancers. There is no suggestion that the organic extracts be used to treat cancers per se.

Notwithstanding the forty-year war on cancer and the deliberate progress which has been made toward improving the prognosis for many types of cancer, cancer remains a killer that continues to terrorize the population. With the recent discoveries of natural plant compounds that have anti-cancer properties, the idea that there might be plant products which will provide even more efficacious anti-cancer compounds has captured the imagination of medical research teams around the world. Therefore, there remains a need for compounds and compositions isolated from natural sources which have anti-cancer and anti-tumor properties.

SUMMARY OF THE INVENTION

The present invention provides a non-fiber composition prepared from an organic extract of psyllium which is anti-tumorigenic. The composition reverses the inhibitory effect of the ras oncogene on gap junctional intercellular communication (GJIC) and the stimulatory effect of the ras oncogene on anchorage independent growth of mammalian cells which have been transformed with the ras oncogene. In other words, the composition both restores gap junctional intercellular communication (GJIC) and inhibits anchorage independent growth of mammalian cells which have been transformed with the ras oncogene. The composition is a useful chemotherapy and chemopreventative agent. The composition was identified using a novel method for determining the anti-tumorigenic potential of a compound or composition.

Therefore, the present invention provides a composition which comprises a mixture of an organic solvent extract of psyllium wherein the mixture is free of fiber of the psyllium and is in a pharmaceutically acceptable carrier. The above composition can comprise the organic solvent extract of psyllium in the organic solvent or the organic solvent extract of psyllium in which the organic extract has been removed prior to mixing with the pharmaceutically acceptable carrier.

The present invention also provides an anti-tumorigenic composition, which comprises an alcohol soluble, non-fiber component of psyllium produced by mixing the psyllium with an alcohol which solublizes the non-fiber component of the psyllium; separating the alcohol soluble, non-fiber component of the psyllium from the fiber of the psyllium to produce the alcohol soluble, non-fiber component of the psyllium; and, admixing with a pharaceutically acceptable carrier. The above composition can comprise the alcohol soluble, non-fiber component of the psyllium in the alcohol or the alcohol soluble, non-fiber component of the psyllium in which the alcohol has been removed prior to mixing with the pharmaceutically acceptable carrier.

In a preferred embodiment of the above compositions, the psyllium is seed husk powder of *Plantago ovata*. In a further embodiment, the organic solvent is an alcohol selected from the group consisting of ethanol and methanol. Preferably, the composition has the property of restoring gap junctional intercellular communication and inhibiting anchorage independent growth in mammalian cells containing a mutated ras gene and displaying unregulated proliferation.

The present invention further provides a method for inhibiting a tumor containing cells, which are incompetent for gap junctional intercellular communication (GJIC), in a patient, which comprises providing to the patient a composition comprising a mixture of an organic solvent extract of psyllium, which is free of fiber of the psyllium and is in a pharmaceutically acceptable carrier, in an amount and for a time sufficient to inhibit the tumor.

Further still, the present invention provides a method for inhibiting a tumor containing cells, which are incompetent for gap junctional intercellular communication (GJIC), in a patient comprising providing to the patient for a time sufficient to inhibit the tumor, which comprises (a) providing an organic solvent soluble, non-fiber component of psyllium produced by mixing the psyllium with an organic solvent which solublizes the non-fiber component of the psyllium; separating the organic solvent soluble, non-fiber component of the psyllium from the fiber component of the psyllium to produce the organic solvent soluble, non-fiber component of the psyllium free of the fiber component; and (b) administering the organic solvent soluble, non-fiber component of psyllium to the patient in an amount sufficient to inhibit the tumor. In a further embodiment, the organic solvent of the organic solvent soluble, non-fiber component of the psyllium free of the fiber component of step (a) is removed to produce a dried non-fiber component of the psyllium free of the fiber component which is mixed with a pharmaceutically acceptable carrier.

In a preferred embodiment of the above methods, the psyllium is seed husk powder of *Plantago ovata*. It is further preferable that the cells comprise a ras mutation, preferably, a ras mutation which renders the cells incompetent for gap junctional intercellular communication (GJIC) incompetent and competent for anchorage independent growth (AIG). In a further embodiment, the organic solvent is an alcohol selected from the group consisting of ethanol and methanol. Preferably, the composition has the property of restoring gap junctional intercellular communication and inhibiting anchorage independent growth in mammalian cells containing a mutated ras gene and displaying unregulated proliferation. Preferably, the patient is a human or a mammal.

Further still, the present invention provides a method for determining whether a compound is anti-tumorigenic, which comprises (a) providing a first and second culture of a monolayer of mammalian cells which are incompetent for gap junctional intercellular communication (GJIC) and competent for anchorage independent growth (AIG) in a culture medium and a third and fourth culture of the cells in a soft agar medium on top of a solid agar medium; (b) adding to the first culture and to the third culture medium containing one or more dilutions of the compound; (c) incubating the first culture for between about 1 to 4 days in the medium containing the compound and the third culture for about 21 days in the medium containing the compound; and (d) determining GJIC of the cells in the first and second cultures and determining AIG of the mammalian cells in the third and fourth cultures wherein an increase in GJIC between the first and second cultures and a decrease in AIG between the third and fourth cultures indicates that the compound is anti-tumorigenic.

In a preferred embodiment of the above method, the GJIC is determined by a scrape-loading and dye transfer method wherein a membrane impermeable fluorescent dye is added to the cell, one or more parallel scrapes are made in the cell monolayer to allow passage of the membrane impermeable dye into cells ruptured by the scrapes, removing the dye which has not entered the ruptured cells, and observing migration of the dye to cells adjacent to the ruptured cells under an energy source to induce the dye to fluoresce. If is further preferable that the AIG is determined by staining the cells with a dye and counting colonies formed by the cells and measuring the size of the colonies.

In a further embodiment of the above method, the mammalian cells are selected from the group consisting of rat cells, mouse cells, and human cells. Preferably, the mammalian cells contain a mutated ras gene, preferably, a ras mutation which renders the cells incompetent for gap junctional intercellular communication (GJIC) incompetent and competent for anchorage independent growth (AIG). In a further embodiment, the mammalian cells are WB-F344 cells transfected with a mutated ras gene.

In a further embodiment of the present invention, a method is provided for restoring gap junctional intercellular communication (GJIC) in the cells of a mammal, including humans, which comprises (a) determining whether the cells of the mammal comprises a mutation in the ras gene; and (b) administering to mammals who have been determined in step (a) to have the mutation in the ras gene a composition comprising seed husk powder of psyllium in an amount sufficient to restore the GJIC. Preferably, the seed husk powder is from *Plantago ovata*.

In a further embodiment of the present invention, a method is provided for restoring gap junctional intercellular communication (GJIC) in the cells of a mammal, including humans, which comprises (a) determining whether the cells of the mammal comprises a mutation in the ras gene; and (b) administering to mammals who have been determined in step (a) to have the mutation in the ras gene a composition comprising an alcohol soluble extract of seed husk powder of psyllium which is free of fiber of the psyllium in an amount sufficient to restore the GJIC. Preferably, the seed husk powder is from *Plantago ovata*. It is further preferable that the composition comprises the alcohol soluble extract of seed husk powder of psyllium which is free of fiber of the psyllium and a pharmaceutically acceptable carrier.

OBJECTS

It is an object of the present invention to provide an in vitro method for identifying compounds and compositions which have anti-tumorigenic potential.

It is a further object of the present invention to provide a composition with anti-tumorigenic effects.

These and other objects of the present invention will become increasingly apparent with reference to the following drawings and preferred embodiments.

DESCRIPTION OF THE DRAWINGS

FIG. 8b shows a densitometry analysis of the ras protein bands in shown in FIG. 8a.

DETAILED DESCRIPTION OF THE INVENTION

Figure 1A:
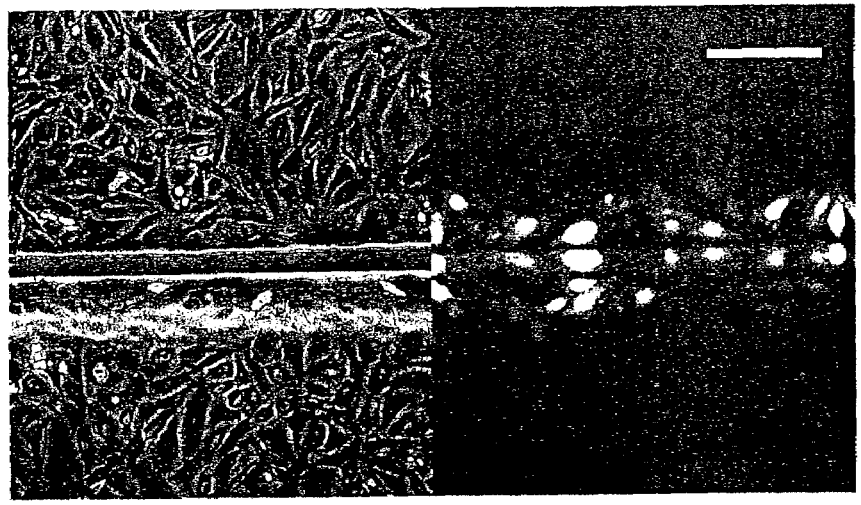
FIG. 1a is a control which shows that treating WB-Ha-ras cells with ethanol for 48 hours does not the restore GJIC. GJIC was measured using the scrape loading dye transfer technique. Bar inset=50 µm.

All patents, patent applications, government publications, government regulations, and literature references cited in this specification are hereby incorporated herein by reference in their entirety. In case of conflict, the present description, including definitions, will control.

The present invention provides an anti-tumorigenic composition comprising an organic extract of psyllium which is free of the fibers of the psyllium. The composition inhibits unregulated or maglignant proliferation of cells which are incompetent for gap junctional intercellular communication (GJIC) in vitro and in vivo and competent for anchorage independent growth (AIG) in vitro and in vivo. For example, cells in which the ras gene has been mutated to be permanently turned on and the cell contains other mutations such that the combination of the ras mutation and the other mutations renders the cells malignant (incompetent for GJIC and competent for AIG). The anti-tumorigenic activity of the composition of the present invention effects (1) a reversal of ras-induced GJIC incompetence (inhibition) and thus, effects a restoration of GJIC between cells with such ras mutations and between cells with such ras mutations and normal cells and (2) a concomitant decrease in ras-induced competence in or stimulation of AIG and thus, effects an inhibition AIG in the cells with such ras mutations.

About 30% of human cancers are associated with mutations in the ras gene which turn the gene permanently on. More specifically, about 90% of pancreatic cancers, about 50% of colon and lung cancers, 50% of thyroid tumors, and about 30% of liver tumors and myeloid leukemias have mutations in the ras gene which turn the gene permanently on. Therefore, abrogating the effect of such ras mutations is an important objective of current chemotherapies for ras-induced cancers and tumors. The most common chemotherapy methods involve the use of cytotoxic chemicals which are used in an amount which will kill rapidly growing cells such as tumor or cancer cells without also killing more slowly growing normal cells. While these cytotoxic chemicals can effectively cause tumor or cancer remissions, their cytotoxic nature usually produce a wide range of undesirable side effects which limits the amount and length of time these chemicals can be used.

The composition of the present invention provides a novel composition for treating patients (human or other mammals) with tumors or cancers. *Plantago ovata* FORSSK. (*Plantaginaceae*), also known as blond psyllium, indian *plantago*, ispaghula, psyllium, and spongel seeds, contains a variety of known chemicals some which have known biological activities (Phytochemical Database, U.S. Department of Agriculture, ARS, NGRL, Beltsville Agricultural Research Center, Beltsville, Md.). For example, chemicals which have been identified in psyllium but which have unknown biological activities include 4-O-methyl-glucoronic acid, alsobiuronic acid, D-galacturonic acid, D-xylose, DL-alanine, DL-norleucine, DL-valine, various fats, indicamine, L-arabinose, L-asparagine, L-cysteine, L-lysine, L-rhamnose, linolenic acid, planteose, rhamnose, sterols, and uronic acid. Chemicals that have been identified in psyllium and which have known biological activities include aucubin (antibacterial, antidote (amanitin), antiinflammatory, antioxidant, antiprolactin, antistaphylococcic, candidicide, cathartic, diuretic, hepatoprotective, lactagogue, laxative, paralytic, pesticide, rna-inhibitor, uricosuric); behenic-acid (cosmetic); fructose (antialcoholic, antidiabetic, antihangover, antiketotic, antinauseant, laxative, neoplastic, sweetener); galactose (sweetener); glucose (acetylcholinergic, antiedemic, antihepatotoxic, antiketotic, antivaricose, hyperglycemic, memory-enhancer); lignoceric-acid (antihepatotoxic); linoleic-acid (5-alpha-reductase-inhibitor, antianaphylactic, antiarteriosclerotic, antiarthritic, anticoronary, antieczemic, antifibrinolytic, antigranular, antihistaminic, antiinflammatory, antileukotriene-d4, antimenorrhagic, antims, antiprostatitic, cancer-preventive, carcinogenic, hepatoprotective, hypocholesterolemic, immunomodulator, insectifuge, metastatic, nematicide); mucilage (cancer-preventive, demulcent); myristic-acid (cancer-preventive, cosmetic, hypercholesterolemic gas, lubricant, nematicide); oleic-acid (5-alpha-reductase-inhibitor, allergenic, anemiagenic, antiinflammatory, antileukotriene-d4, cancer-preventive, choleretic, dermatitigenic, flavor fema 1–30, hypocholesterolemic, insectifuge, irritant m11, percutaneostimulant, perfumery); palmitic-acid (5-alpha-reductase-inhibitor, antifibrinolytic, flavor fema 1, hemolytic, hypercholesterolemic, lubricant, nematicide, pesticide, soap); stearic-acid (5-alpha-reductase-inhibitor, cosmetic, flavor fema 2–4,000, hypocholesterolemic, lubricant, perfumery, propecic, suppository); sucrose plant (aggregant, antihiccup, antiophthalmic, antioxidant, atherogenic, collyrium, demulcent, flatugenic, hypercholesterolemic, preservative, sweetener, triglycerigenic, uricogenic, vulnerary); tannins (anthelmintic, antibacterial, anticancer, anticariogenic, antidiarrheic, antidysenteric, antihepatotoxic, antihiv, antihypertensive, antilipolytic, antimutagenic, antinephritic, antiophidic, antioxidant, antiradicular, antirenitic, antitumor, antitumor-promoter, antiulcer, antiviral, cancer-preventive, carcinogenic, chelator, cyclooxygenase-inhibitor, glucosyl-transferase-inhibitor, hepatoprotective, immunosuppressant, lipoxygenase-inhibitor, mao-inhibitor, ornithine-decarboxylase-inhibitor, pesticide, psychotropic, xanthine-oxidase-inhibitor); tyrosine (antidepressant, antiencephalopathic, antiparkinsonian, antiphenylketonuric, antiulcer, cancer-preventive, monoamine-precursor); valine (antiencephalopathic, essential, flavor fema 1,000–2,000); and, xylose (antidiabetic, diagnostic mar, dye). Because of the ability of the composition of the present invention to restore GJIC and inhibit AIG in proliferating cells with ras mutations, the composition of the present invention is useful in chemotherapies and chemopreventative strategies for treating cancers and tumors induced by mutations in ras.

Chemotherapeutic uses include not only treatments which rely solely on the effects of the composition of the present invention but also include treatments where the composition is mixed with one or more cytotoxic chemicals useful for chemotherapy treatments. The composition enables the cytotoxic chemicals to be used at concentrations which are less apt to cause unwanted side effects. The composition can also be used with chemotherapy enhancing drugs which are often mixed with chemotherapy chemicals to augment the chemotherapy treatment. Such drugs include statins such as lovastatin, simvastatin, pravastatin, and the like and COX-2 inhibitors such as nimesolide, lodine, celecoxib, rofecoxib, and the like. Thus, chemotherapeutic compositions comprising the composition of the present invention include the composition of the present invention, mixtures of the composition with cytotoxic chemicals, mixtures of the composition with cytotoxic chemicals and enhancing drugs, and mixtures of the composition with chemotherapy enhancing drugs.

Chemopreventive uses for the composition of the present invention include use as a nutraceutical or dietary supplement for use by persons who may have cells which are predisposed to develop a cancer or tumor which is inducible by one or more mutations in the ras gene. Such persons include those who have cells comprising a mutated ras gene but not mutations in one or more other genes which are associated with cancers or tumors but which would render the cells malignant if mutated or persons who have cells comprising one or more mutations in genes associated with cancers or tumors but do not yet have mutations in the ras gene. The composition can also be used by any other person who wishes to reduce the risk of developing a cancer or tumor which is inducible by mutations in the ras gene. In many cases, it is most likely that persons predisposed to develop a ras-inducible cancer or tumor would need to ingest the composition on a daily basis. A preferred method of use of the composition as a nutriceutical is to test the person or patient for cells which contain a ras mutation and then provide the composition to the person or patient.

The composition of the present invention is prepared by extracting psyllium seed husk powder with an organic solvent such as ethanol or methanol, preferably ethanol, to produce an organic extract. The organic extract is then filtered to remove fibers and other components not soluble in the organic solvent. A Whatman #1 filter paper or the like is sufficient to filter the organic extract. Next, the organic solvent is removed from the filtrate by evaporation to produce a dried form of the composition. The evaporation can be performed under reduced or normal pressure, at room temperature or with mild heating, or combinations thereof. The dried composition can be dissolved or suspended in a an organic or aqueous solvent or liquid carrier to provide the composition as a solution or suspension which can further include chemotherapeutic chemicals, drugs, nutriceuticals, and mixtures thereof. The dried composition can be compounded with a pharmaceutically acceptable carrier. The dried composition can be admixed with one or more chemotherapeutic chemicals, drugs, nutriceuticals, and mixtures thereof and the admixture compounded with a pharmaceutically acceptable carrier or dissolved in a solvent. In general, ten grams of psyllium seed husk powder will provide about 100 mg of the dried composition.

For chemotherapeutic use in patients who have a ras-induced cancer or tumor, the composition is provided to the patient in a pharmaceutically acceptable carrier at a dose which is sufficient to restore GJIC and inhibit AIG in the cells comprising the cancer or tumor. While the dose may be dependent on the particular cancer or tumor afflicting the patient, in many applications, the dose provides the composition to the cancer or tumor cells at a concentration of between about 5 μg/mL and 100 μg/mL, preferably between about 25 to 75 μg/mL. Furthermore, the composition can include one or more chemotherapy chemicals and/or enhancing drugs for augmenting chemotherapy treatments such as statins or COX-2 inhibitors. When provided in dried form, the composition is processed with pharmaceutical carrier substances by methods well known in the art such as by means of conventional mixing, granulating, coating, suspending and encapsulating methods, into the customary preparations for oral or rectal administration. Thus, preparations for oral application can be obtained by combining the composition with solid pharmaceutical carriers; optionally granulating the resulting mixture; and processing the mixture or granulate, if desired and/or optionally after the addition of suitable auxiliaries, into the form of tablets or dragee cores.

Suitable pharmaceutical carriers for solid preparations are, in particular, fillers such as sugar, for example, lactose, saccharose, mannitol or sorbitol, cellulose preparations and/or calcium phosphates, for example, tricalcium phosphate or calcium hydrogen phosphate; also binding agents, such as starch paste, with the use, for example, of maize, wheat, rice or potato starch, gelatine, tragacanth, methyl cellulose, hydroxypropylmethyl cellulose, sodium carboxymethyl cellulose and/or polyvinylpyrrolidone, esters of polyacrylates or polymethacrylates with partially free functional groups; and/or, if required, effervescent agents, such as the above-mentioned starches, also carboxymethyl starch, cross-linked polyvinylpyrrolidone, agar, or alginic acid or a salt thereof, such as sodium alginate. Auxiliaries are primarily flow-regulating agents and lubricating agents, for example, silicic acid, talcum, stearic acid or salts thereof, such as magnesium stearate or calcium stearate. Dragee cores are provided with suitable coatings, optionally resistant to gastric juices, whereby there are used, inter alia, concentrated sugar solutions optionally containing gum arabic, talcum, polyvinylpyrrolidone, and/or titanium dioxide, lacquer solutions in aqueous solvents or, for producing coatings resistant to stomach juices, solutions of esters of polyacrylates or polymethacrylates having partially free functional groups, or of suitable cellulose preparations such as acetylcellulose phthalate or hydroxypropylmethylcellulose phthalate, with or without suitable softeners such as phthalic acid ester or triacetin. Dyestuffs or pigments may be added to the tablets or dragee coatings, for example for identification or marking of the various doses of active ingredient.

Anticancer or antitumor preparations comprising the composition which can be administered orally further include hard gelatine capsules, as well as hard or soft closed capsules made from gelatine and, if required, a softener such as glycerin or sorbitol. The hard gelatine capsules can contain the composition in the form of a granulate, for example in admixture with fillers such as maize starch, optionally granulated wheat starch, binders or lubricants such as talcum, magnesium stearate or colloidal silicic acid, and optionally stabilizers. In closed capsules, the composition is in the form of a powder or granulate; or it is preferably present in the form of a suspension in suitable solvent, whereby for stabilizing the suspensions there can be added, for example, glycerin monostearate.

Other anticancer or antitumor preparations to be administered orally are, for example, aqueous solutions or suspensions prepared in the usual manner, which solutions or suspensions contain the composition in the dissolved or suspended form and at a concentration rendering a single dose sufficient. The aqueous solutions or suspensions either contain at most small amounts of stabilizers and/or flavoring substances, for example, sweetening agents such as saccharin-sodium, or as syrups contain a certain amount of sugar and/or sorbitol or similar substances. Also suitable are, for example, concentrates or concentrated suspensions for the preparation of shakes. Such concentrates can also be packed in single-dose amounts.

Suitable anticancer or antitumor preparations for rectal administration are, for example, suppositories consisting of a mixture of the composition with a suppository foundation substance. Such substances are, in particular, natural or synthetic triglyceride mixtures. Also suitable are gelatine rectal capsules consisting of a suspension of the composition in a foundation substance. Suitable foundation substances are, for example, liquid triglycerides, of higher or, in particular, medium saturated fatty acids.

Likewise of particular interest are preparations containing the finely ground composition, preferably having a median particle size of 5 μm or less, in admixture with a starch, especially with maize starch or wheat starch, also, for example, with potato starch or rice starch. They are produced preferably by means of a brief mixing in a high-speed mixer having a propeller-like, sharp-edged stirring device, for example with a mixing time of between 3 and 10 minutes, and in the case of larger amounts of constituents with cooling if necessary. In this mixing process, the particles of the composition are uniformly deposited, with a continuing reduction of the size of some particles, onto the starch particles. The mixtures mentioned can be processed with the customary, for example, the aforementioned, auxiliaries into the form of solid dosage units; i.e., pressed for example into the form of tablets or dragees or filled into capsules. They can however also be used directly, or after the addition of auxiliaries, for example, pharmaceutically acceptable wetting agents and distributing agents, such as esters of polyoxyethylene sorbitans with higher fatty acids or sodium lauryl sulphate, and/or flavoring substances, as concentrates for the preparation of aqueous suspensions, for example, with about 5- to 20-fold amount of water. Instead of combining the composition/starch mixture with a surface-active substance or with other auxiliaries, these substances may also be added to the water used to prepare the suspension. The concentrates for producing suspensions, consisting of the composition/starch mixtures and optionally auxiliaries, can be packed in single-dose amounts, if required in an airtight and moisture-proof manner.

In addition, the composition can be administered to a patient intraperitoneally, intranasally, subcutaneously, or intravenously. In general, for intraperitoneal, intranasal, subcutaneous, or intravenous administration, the composition is provided by dissolving, suspending or emulsifying it in an aqueous or nonaqueous solvent, such as vegetable or other similar oils, synthetic aliphatic acid glycerides, esters of higher aliphatic acids or propylene glycol, alcohols such as ethanol; and if desired, with conventional additives such as solubilizers, isotonic agents, suspending agents, emulsifying agents, stabilizers and preservatives. Preferably, the composition is provided as a component in a composition acceptable for intraperitoneal, subcutaneous, or intravenous use in warm-blooded animals or humans. For example, such compositions can comprise a physiologically acceptable solution such as a buffered phosphate salt solution as a carrier for the composition. Preferably, the solution is at a physiological pH. In particular embodiments, the composition is injected directly into the tumor or perfused through the tumor by intravenous administration.

Anticancer or antitumor preparations according to the present invention comprise the composition at a concentration suitable for administration to warm-blooded animals or humans which concentration is, depending on the mode of administration, between about 0.3% and 95%, preferably between about 2.5% and 90%. In the case of suspensions, the concentration is usually not higher than 30%, preferably about 2.5%; and conversely in the case of tablets, dragees and capsules with the composition, the concentration is preferably not lower than about 0.3%, in order to ensure an easy ingestion of the required doses of the composition.

The treatment of cancers and tumors in patients with the preparations comprising the composition is carried out preferably by one or more administrations of a dose of the composition which over time is sufficient to substantially inhibit the cancer or tumor, that is to say, an amount which is sufficient to cause complete or partial remission of the cancer or tumor. If required, the doses can be administered daily or divided into several partial doses which are administered at intervals of several hours. In particular cases, the preparations can be used prior to, in conjunction with, or following one or more other anticancer or antitumor therapies such as radiation or chemotherapy, or in conjunction with surgical procedures for removing cancers or tumors. The administered dose of the composition is dependent both on the patient (species of warm-blooded animal or human) to be treated, the general condition of the patient to be treated, and on the type of cancer or tumor to be treated.

The composition of the present invention appears to be preferentially effective in restoring GJIC and inhibiting AIG in cells containing a ras mutation but not cells containing mutations in the neu or src genes, or cells containing a myc-ras mutations. Therefore, prior to treating a patient with a cancer or tumor with the composition, it is prudent to determine whether the cancer or tumor cells is induced by a ras mutation and not by a neu, src, or myc-ras mutations. Immunohistochemical methods are well known for distinguishing the above mutations. Thus, it is preferable to determine whether the cells comprising the cancer or tumor contain a ras mutation.

For chemopreventive use in patients or mammals, including humans, who might be predisposed to developing a ras-induced cancer or tumor and other individuals, the composition is provided either as a component of an aqueous solution or in a pharmaceutically acceptable carrier at a dose which is sufficient to restore GJIC and inhibit AIG in the cells comprising the cancer or tumor. The pharmaceutically acceptable carrier can be any one of the above described carriers. In addition, the composition can be admixed with nutrients which have cancer and tumor inhibiting characteristics such as bee propolis, anthracyanins, lignins, various antioxidants, and the like, or other nutrients which are healthy or necessary for maintaining or establishing health in an individual such as vitamins, enzymes, fats, minerals, and mixtures thereof. The most common means for administering the composition for chemopreventative purposes is orally thus, for most applications, the composition is provided in tablets or capsules such as those described above, in an aqueous solution, or as a powder for mixing with an aqueous solution.

In particular embodiments, the present invention further provides a method for restoring GJIC in cells of a patient or mammal, including humans, which have been identified as having cells which are incompetent in GJIC. The method involves the steps of removing a sample of cells from a patient or mammal, including humans, and testing the cells to determine whether the cells have a mutation in the ras gene. In some embodiments, this can be done immunohistochemically using methods well known in the art and in other embodiments, the DNA from the cells can be isolated and analyzed for mutations in the ras gene by polymerase chain reaction, restriction fragment length polymorphisms, or the like. In further embodiments, the cells can be tested for GJIC incompetence, and AIG competence. For a patient whose cells contain a ras mutation and are GJIC incompetent and AIG competence in vitro. For patients or mammals, including humans determined to contain the ras mutation, the patient or mammal, including humans, is administered a composition comprising an alcohol soluble extract of seed husk powder of psyllium which is free of fiber of the psyllium in an amount sufficient to restore the GJIC. Preferably, the composition comprises the alcohol soluble extract of seed husk powder of psyllium which is free of fiber of the psyllium and a pharmaceutically acceptable carrier. Alternatively, the patient or mammal, including humans is administered a composition comprising seed husk powder of psyllium in an amount sufficient to restore the GJIC psyllium seed husk powder to restore GJIC. The above method is useful for treating cancers and tumors in a patient or mammal, including humans, and for inhibiting formation of cancers or tumors in a patient or mammal, including humans.

The present invention further provides an in vitro method for determining whether a compound or composition has the ability to restore GJIC and inhibit AIG in a cell line which is GJIC incompetent and AIG competent. An example of such a cell line is a cell line wherein the cells comprise a ras mutation which renders the cells GJIC incompetent (inhibits GJIC) and renders the cells AIG competent (stimulates AIG). The method entails two separate assays: the first assay measures restoration of GJIC and the second assay measures inhibition of AIG. The above method enabled the discovery of the composition of the present invention. The above method can be used to determine which of the compounds or mixture of compounds which have been identified above might be capable of restoring GJIC and inhibiting AIG.

In the first assay, the cell line is incubated in tissue culture plates in media containing one or more dilutions of the test compound. After about 48 hours, the cells are assayed for restoration of GJIC using the scrape-load dye technique described in Weis et al., Environ. Heath Perspect. 106: 17–22 (1998) and El-Fouly et al., Exp. Cell Res. 168: 422–430 (1987). Briefly, following exposure to the test compound, the cells were washed three times with a buffered solution such as phosphate buffered saline (PBS). A fluorescent dye which cell membrane impermeable is dissolved in the same buffered solution at a concentration of about 1 mg/mL is added to the cells. Three parallel scrapes are then made in the cell monolayer on the plate using a surgical blade to allow passage of the membrane impermeable dye into ruptured cells. After about a three-minute incubation, the cells were washed with buffered solution without the dye to remove extracellular dye and the cells fixed with 4% formalin. Dye migration is visually observed using a fluorescence microscope and compared to controls without the test compound. The distance of dye migration perpendicular to the scrape (that is, between adjacent cells linked only by gap junctions) represents the ability of cells to communicate via GJIC.

In the second assay, about a thousand cells of the cell line in agarose medium are plated onto the top of 0.5% agarose medium in a tissue culture plate. After 1 day, medium containing the test compound is added on top of the agar plates. The medium containing the test compound is renewed every other day. At the end of 3 weeks, colonies are stained overnight with 1 mg/mL of 2-(p-iodophenyl)-3-(nitrophenyl)-5-phenyl-tetrazolium chloride at 37° C. Inhibition of anchorage independent growth is determined by observing a lack of colony growth and/or small size of the colonies compared to controls without the test compound.

The above method requires a cell line which is GJIC deficient and AIG enabled. A preferred cell line has a ras mutation which has rendered the cells GJIC incompetent and AIG competent. For example, the mouse WB-F344 cell line, an immortal cell line which is available from the Health Science Research Resources Bank, Rinku-minamihama 2–11, Sennan-shi, Osaka, Japan under accession number JCRB0193, can be transfected with a recombinant retrovirus vector comprising the v-Ha-ras oncogene and a neomycin-resistant marker as described in de-Feijter et al., Mol. Carcinog. 3: 54–67 (1990) to produce a WB-H-ras cell line which is GJIC deficient and AIG enabled. The WB-H-ras cell line has been available by name from Michigan State University, Department of Pediatrics & Human Development, 243 National Food Safety & Toxicology Center, East Lansing, Mich., since 1990.

A method for identifying compounds which restore GJIC but without consideration of whether the compounds affect AIG (that is, a method which includes the first assay and not the second assay) can use the above WB-H-ras cell line or the HPDE6c7 cell line. The human pancreatic ductal epithelial clone 7 cell line (HPDE6c7) is a clonal population of immortalized HPDE cells derived from HPDE cells which had been immortalized by transfecting the cells with an amphotrophic retrovirus containing human papilloma virus (HPV) 16 genes E6 and E7. The cell line is incompetent for GJIC but shows anchorage dependent growth in vitro. The cell line has been disclosed in U.S. patent application Ser. No. 10/135,801 to Trosko et al., filed Apr. 30, 2002, and deposited under the terms of the Budapest Treaty at the American Type Culture Collection, 10801 University Boulevard, Manassas, Va. as ATCC PTA-4441.

The following examples are intended to promote a further understanding of the present invention.

EXAMPLE 1

This example illustrates the discovery of the anti-tumorigenic, alcohol-soluble, fiber-free psyllium seed husk composition of the present invention.

Ethanol extraction of psyllium seed husk was performed as follows. A 10 g sample of psyllium seed husk powder (GNC, Pittsburgh, Pa.) was extracted with 20 mL of pure ethanol at room temperature and then filtered through a Whatman #1 filter. The residue was washed additional two times with 20 mL of ethanol. Ethanol filtrates were combined and evaporated to dryness using a rotary evaporator at 37° C. The yield was 125±25 mg dried weight from 10 g of the material.

Cells were treated with psyllium extract as follows. WB-Ha-ras cells ($5 \times 10^4$) were plated in 35-mm culture plates (Corning Inc., Corning, N.Y.) with 2 mL of Dulbecco's modified Eagle's medium (DMEM, Formula No. 78–5470EF, GIBCO Laboratories, Grand Island, N.Y.) containing 5% fetal bovine serum (5% FBS-DMEM) and cultured overnight. Cells were treated with samples of psyllium (as 10 µL of ethanol solution) in 2 mL of 5% FBS-DMEM.

The normal WB-F344 rat liver epithelial cell line was obtained from Drs. J. W. Grisham and M. S. Tsao of the University of North Carolina (Chapel Hill, N.C.). The cell line is an immortalized, diploid non-tumorigenic cell line derived from a male rat that have retained classic liver oval cell markers (Tsao et al., Exp. Cell Res. 154: 38–52 (1984)). The cell line is also available from the Health Science Research Resources Bank, Rinku-minamihama 2–11, Sennan-shi, Osaka, Japan under accession number JCRB0193. The WB-Ha-ras cell line was developed from the transfection of WB-F344 cell line with a retroviral vector containing the v-Ha-ras oncogene and a neomycin-resistant marker as described in de-Feijter et al., Mol. Carcinog. 3: 54–67 (1990). These ras-transformed cells were characterized as GJIC deficient in vitro and as tumorigenic in vivo (de-Feijter et al., Mol. Carcinog. 3: 54–67 (1990)).

The Scrape Load-Dye transfer Assay for determining gap junctional intercellular communication (GJIC) was performed as follows. GJIC was measured using the scrape loading dye transfer technique (Weis et al., Environ. Heath Perspect. 106: 17–22 (1998); El-Fouly et al., Exp. Cell Res. 168: 422–430 (1987)). Briefly, following exposure to psyllium, the cells were washed three times with phosphate buffered saline (PBS). The fluorescent dye, Lucifer yellow (Sigma, St. Louis, Mo.) dissolved in PBS (1 mg/mL) was added to the cells. Three parallel scrapes were made in the cell monolayer using a surgical blade to allow passage of the membrane impermeable dye into ruptured cells. After a three-min incubation, the cells were washed with PBS to remove extracellular dye and were fixed with 4% formalin. Dye migration was observed and digitally photographed at 200× using a Nikon epifluorescence microscope illuminated with an Osram HBO 200W lamp and equipped with a COHU video camera. The program GEL-EXPERT (Nucleotech, San Mateo, Calif.) was used to quantify GJIC by determining the distance of dye migration. The distance of dye migration perpendicular to the scrape (that is, between adjacent cells linked only by gap junctions) represents the ability of cells to communicate via GJIC. GJIC activity was calculated as the fraction of the solvent control, all treatments were tested in triplicate.

Western blots were performed as follows. Proteins were extracted with 20% SDS solution according to the method reported in (Trosko et al., Methods 20: 245–264 (2000)). The protein content was determined with the DC assay kit (Bio-Rad Corp., Richmond, Calif.). The proteins (15 µg) were separated on 12.5% SDS-PAGE (Laemmli, Nature 227: 680–685 (1970)) and electrophoretically transferred from the gel to PVDF membranes (Millipore Corp, Bedford, Mass.) (Upham et al., Carcinog. 18: 37–42 (1997)). Connexin43, ras and Erk were detected with anti-connexin 43 (Zymed, South San Francisco, Calif.), anti-pan-ras (Ab-2) monoclonal antibody (Oncogene Research Products, Boston, Mass.), and anti-Erk (total and phosphospecific, New England Biolabs, Beverly, Mass.), respectively, using horseradish peroxidase-conjugated secondary antibody (New England Biolabs, Beverly, Mass.), and then observed with super signal west dura extended duration substrate (Pierce, Rockford, Ill.) and ECL detection kit (Amersham, Life Sci, Denver, Colo.).

Immunofluorescence staining of Connexin 43 and Ras 21 was as follows. WB-Ha-ras cells ($2 \times 10^4$) were plated in a 4-well glass attached chamber slide (Nalge Nunc International, Naperville, Ill.) with 1 mL of 5% FBS-DMEM and cultured overnight. A 10 µL aliquot of ethanol extract was added to the cell culture medium, and then incubated for an additional 48 hours. After the incubation period, cells were washed with phosphate buffered saline (PBS), 3 times, and then fixed with 3.5% formaldehyde (30 minutes) and washed once with PBS; permeabilized the membrane with 0.05% saponin/PBS (30 minutes) and then washed once with PBS. After the cells were fixed they-were blocked with 10% goat serum (Sigma, St. Louis, Mo.) in PBS for 1 hour, and then treated with anti-connexin 43 or anti-Ras 21 antibody diluted 1:100 in 1% goat serum in PBS, and incubated on a shaker at 4° C. for 12 hours. The secondary antibody was a Cy3-conjugated rat or mouse antibody IgG (Jackson Immuno Research Laboratories, Inc., West Grove, Pa.), which was diluted 1/200 in 1% goat serum in PBS and incubated in the dark on a shaker at room temperature for 1 hour. The cells were then washed with PBS and mounted with a cover slip using POLY-AQUAMOUNT (Polysciences, Inc., Washington, Pa.). Microscopic images were digitally obtained from an epifluorescence microscope equipped with a CCD camera (Nikon, Tokyo, Japan).

Anchorage independent growth (AIG) assays were performed as follows. A thousand cells in 3.0 mL of 0.33% agarose medium were plated onto the top of 3.0 mL 0.5% agarose medium. After 1 day, 3 mL of medium containing psyllium was added on top of these agar plates and this medium was renewed every other day. At the end of 3 weeks, colonies were stained overnight with 1 mg/mL of 2-(p-iodophenyl)-3-(nitrophenyl)-5-phenyl-tetrazolium chloride at 37° C.

The composition of the present invention restores gap junction intercellular communication (GJIC) in GJIC deficient cells. The WB-Ha-ras cell line has reduced GJIC as compared to the normal WB cell line (de-Feijter et al., Mol. Carcinog. 3: 54–67 (1990)), and the addition of either the crude powder or the ethanol extract greatly increased GJIC to levels comparable to the normal cells as shown by FIGS.

Figure 1B:
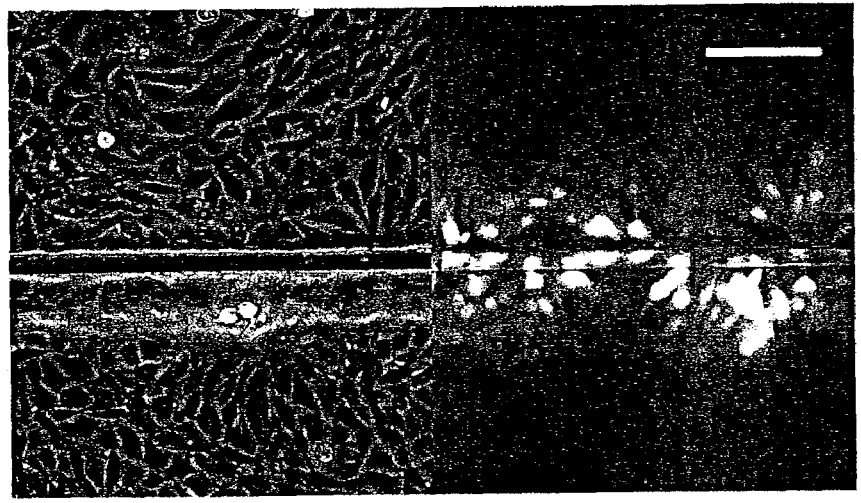
FIG. 1b shows that treating WB-Ha-ras cells with 1.5 mg/mL of crude psyllium seed husk powder for 48 hours restored GJIC. GJIC was measured using the scrape loading dye transfer technique. Bar inset=50 µm.
Figure 1C:
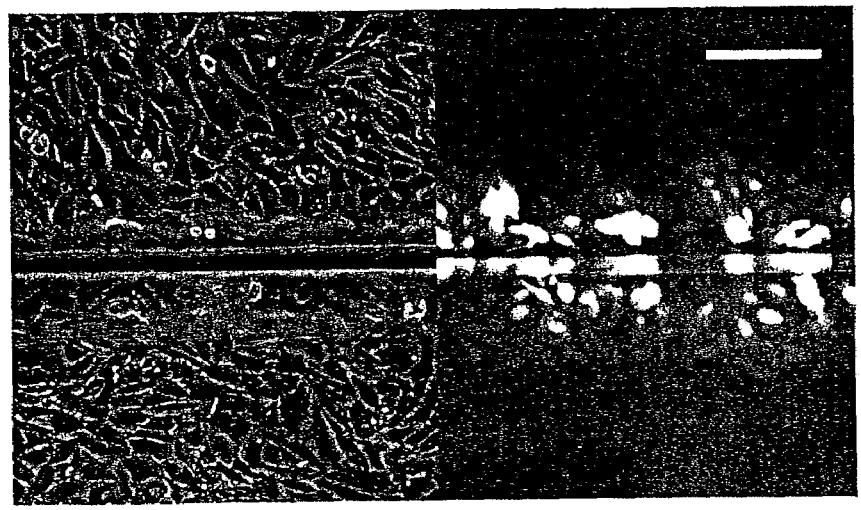
FIG. 1c shows that treating WB-Ha-ras cells with 50 µg/mL EtOH extract prepared from crude psyllium seed husk powder for 48 hours restored GJIC. GJIC was measured using the scrape loading dye transfer technique. Bar inset=50 µm.

1a to 1c. FIG. 1a shows untreated cells and the absence of GJIC. However, GJIC was restored to the cells when the cells were incubated with crude powder (FIG. 1b) or ethanol extract (FIG. 1c). No difference between the crude and ethanol extract, which was filtered through Whatman #1 paper, was observed suggesting that the result was not purely a fiber effect.

Figure 2:
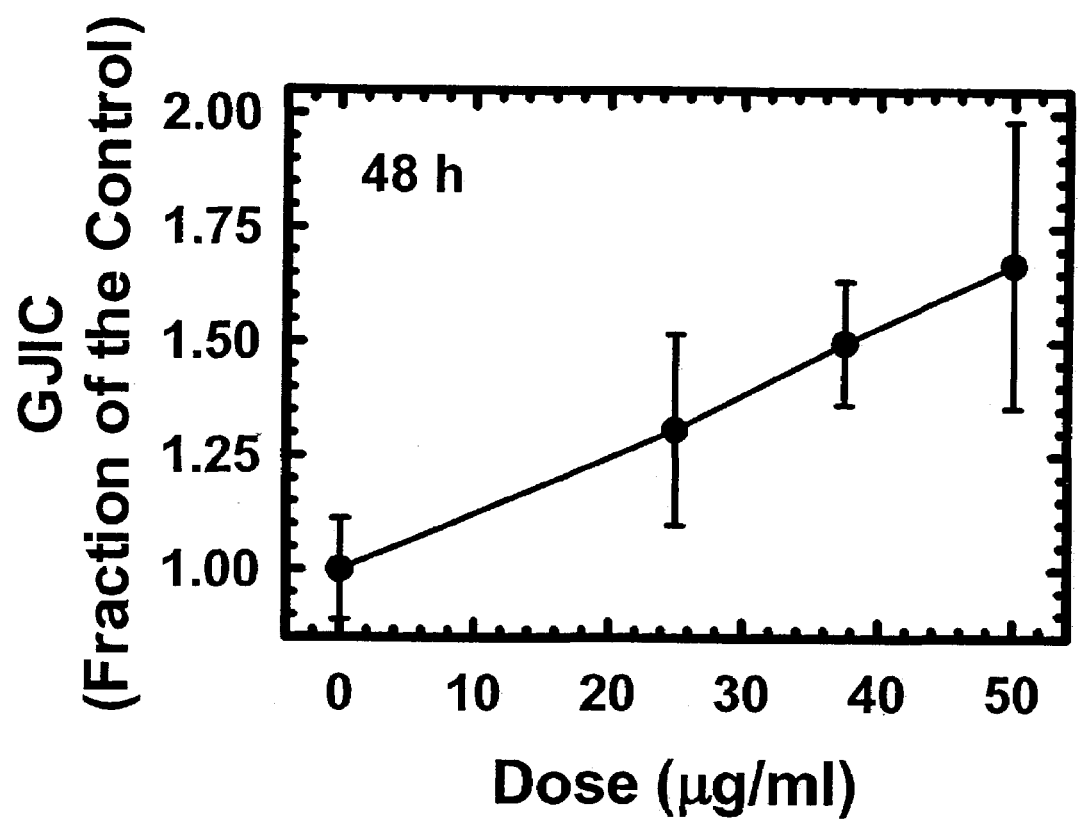
FIG. 2 shows the dose response of psyllium induced restoration of GJIC in WB-Ha-ras cells. The cells were treated for 48 h with the ethanol extract from the seed husk of psyllium. GJIC was measured using the scrape loading dye transfer technique. Each value represents an average of 3 replicates±standard deviation.
Figure 3A:
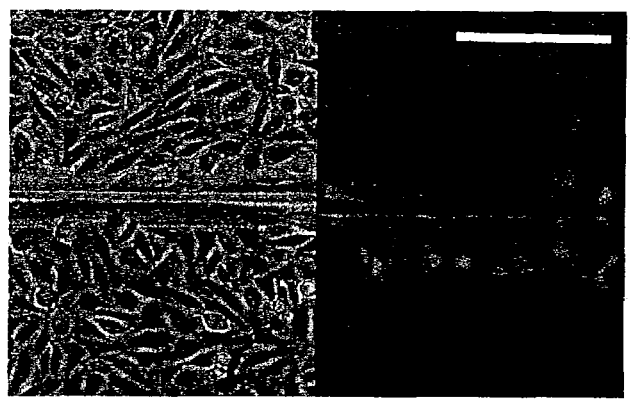
FIG. 3a is a control showing non-GJIC in WB-Ha-ras cells. The cells were treated for 48 hours with ethanol. GJIC was measured using the scrape loading dye transfer technique. Bar inset=50 µm.
Figure 3B:
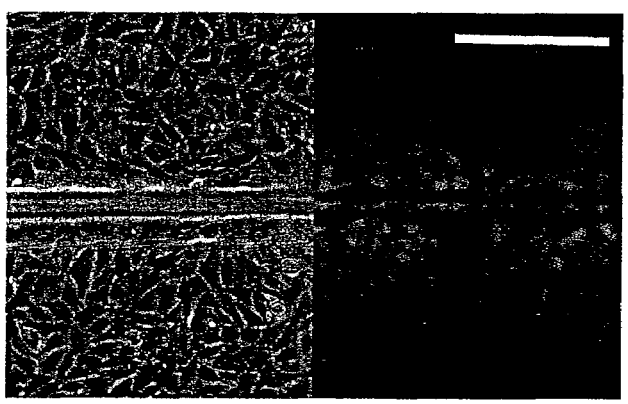
FIG. 3b shows the efficacy of psyllium-induced restoration of GJIC (48 hours) in WB-Ha-ras cells treated for 48 hours with the crude powder of the seed husk of psyllium (1.5 mg/mL) from Vitamin world (lot 4920401; Expiration 8/2003). GJIC was measured using the scrape loading dye transfer technique. Bar inset=50 µm.
Figure 3C:
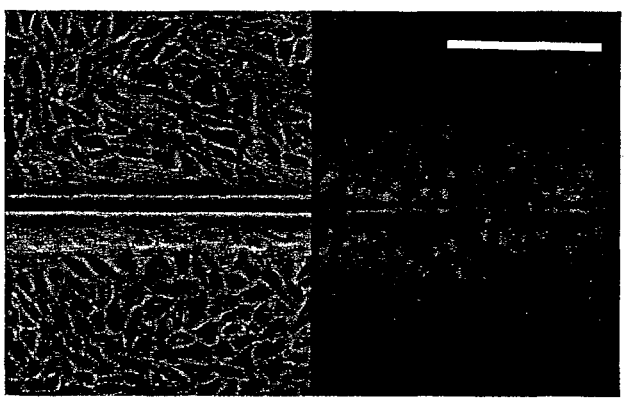
FIG. 3c shows the efficacy of psyllium-induced restoration of GJIC (48 hours) in WB-Ha-ras cells treated for 48 hours with the crude powder of the seed husk of psyllium (1.5 mg/mL) from GNC (lot 96808; Expiration 9/2005). GJIC was measured using the scrape loading dye transfer technique. Bar inset=50 µm.
Figure 3D:
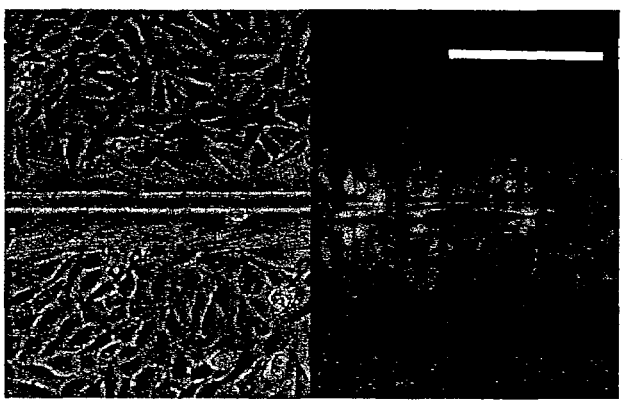
FIG. 3d shows the efficacy of psyllium-induced restoration of GJIC (48 hours) in WB-Ha-ras cells treated for 48 hours with the crude powder of the seed husk of psyllium (1.5 mg/mL) from GNC (lot 88815; Expiration 8/2004). GJIC was measured using the scrape loading dye transfer technique. Bar inset=50 µm.

The restoration of GJIC by the ethanol extract of psyllium seed husk was found to be dose dependent (FIG. 2). This dose response was linear in the dose range used (0 to 50 μg/mL). F FIGS. 3c to 3d show that the effect of psyllium on GJIC in WB-Ha-ras cells was not specific to the commercial source or lot of the psyllium. For example, restoration of GJIC was observed whether the psyllium was obtained from Vitamin World or GNC (compare FIG. 3b to 3c). However, differences in the magnitude of increasing GJIC were seen between two different lots of psyllium from GNC (compare FIG. 3c to 3d). No cytotoxic effect of psyllium was observed up to 1.5 mg/mL of the crude powder of the seed husk of psyllium, and 50 μg/mL in its ethanol extract in WB-Ha-ras cells.

Figure 4:
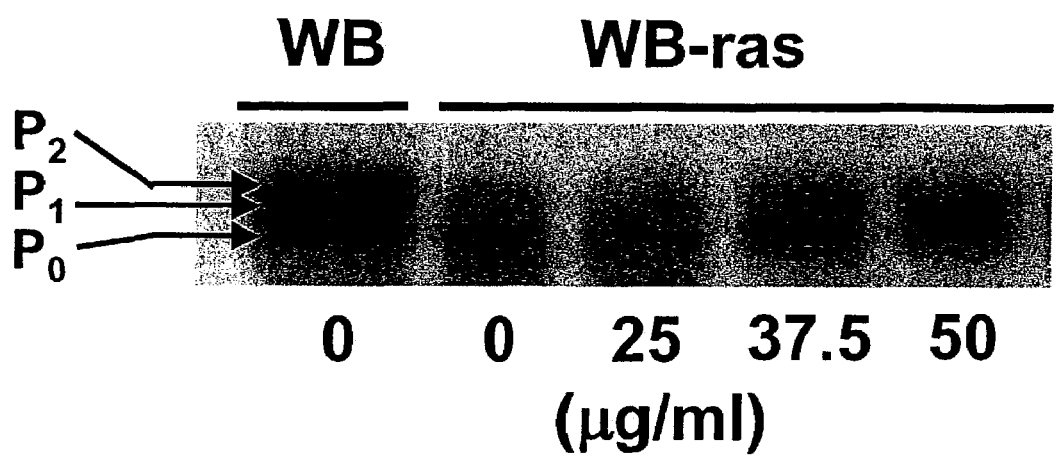
FIG. 4 shows changes in the phosphorylation of connexin 43 in response to different concentrations of the ethanol extract of psyllium seed husk in WB-Ha-ras cells. The cells were treated for 48 hours with the ethanol extract from the seed husk of psyllium. Each lane shows different phosphorylated connexin 43 bands. 15 µg of protein was added to each lane.
Figure 5A:
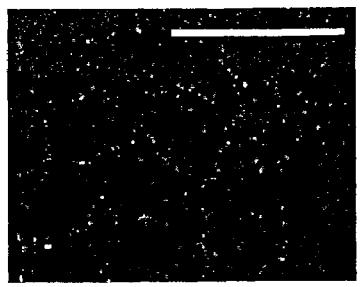
FIG. 5a shows the intracellular localization of connexin 43 in WB cells. Bar inset=20 µm.
Figure 5B:
FIG. 5b shows the intracellular localization of connexin 43 in WB cells without primary antibody. Bar inset=20 µm.
Figure 5C:
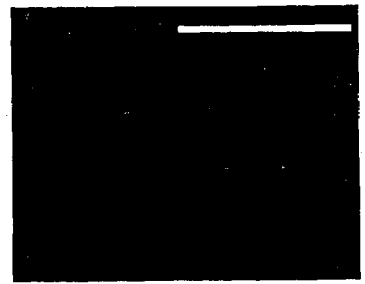
FIG. 5c shows the intracellular localization of connexin 43 in WB cells with C×43 peptide. Bar inset=20 µm.
Figure 5D:
FIG. 5d shows the intracellular localization of connexin 43 in WB-Ha-ras cells with C×43 peptide. Bar inset=20 µm.
Figure 5E:
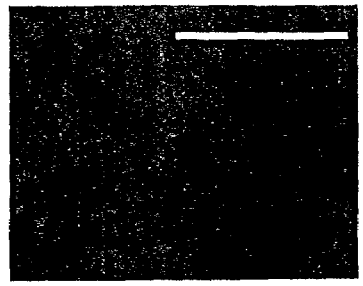
FIG. 5e shows the intracellular localization of connexin 43 in WB-Ha-ras cells. Bar inset=20 µm.
Figure 5F:
FIG. 5f shows the effect of the EtOH extract from psyllium seed husk on the intracellular localization of connexin 43 in WB-Ha-ras cells. The cells were treated for 48 hours with 25 µg/mL of the ethanol extract from the seed husk of psyllium. Bar inset=20 µm.
Figure 5G:
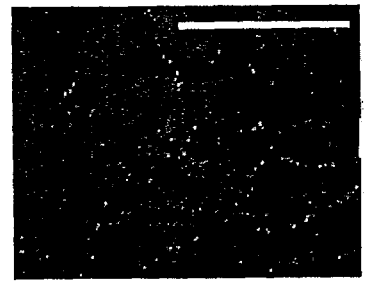
FIG. 5g shows the effect of the EtOH extract from psyllium seed husk on the intracellular localization of connexin 43 in WB-Ha-ras cells. The cells were treated for 48 hours with 37.5 µg/mL of the ethanol extract from the seed husk of psyllium. Bar inset=20 µm.
Figure 5H:
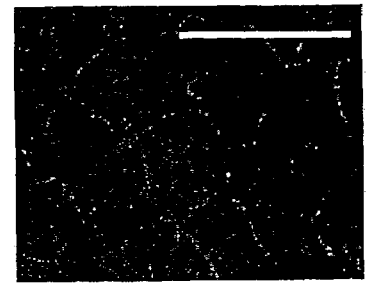
FIG. 5h shows the effect of the EtOH extract from psyllium seed husk on the intracellular localization of connexin 43 in WB-Ha-ras cells. The cells were treated for 48 hours with 50 µg/mL of the ethanol extract from the seed husk of psyllium. Bar inset=20 µm.
Figure 6A:
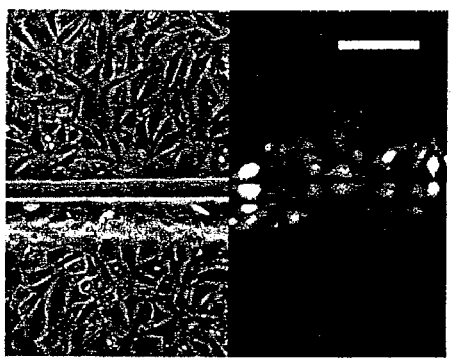
FIG. 6a shows the GJIC in WB-Ha-ras cells. GJIC was measured using the scrape loading dye transfer technique. Bar inset=50 µm.
Figure 6E:
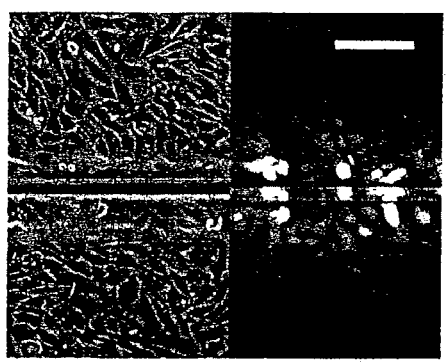
FIG. 6e shows the GJIC in WB cells transformed with src (WB-src cells). GJIC was measured using the scrape loading dye transfer technique. Bar inset=50 µm.
Figure 6B:
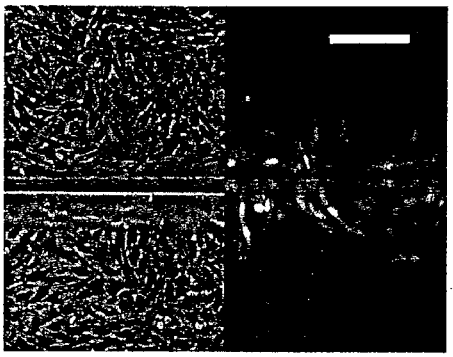
FIG. 6b shows effect of the ethanol extract from psyllium seed husk on GJIC in WB-Ha-ras cells. The cells were treated for 48 hours with 50 µg/mL of the ethanol extract from the seed husk of psyllium. GJIC was measured using the scrape loading dye transfer technique. Bar inset=50 µm.
Figure 6F:
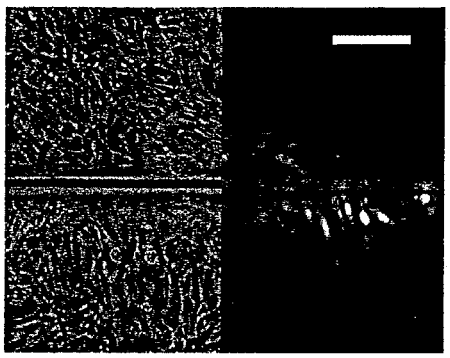
FIG. 6f shows effect of the ethanol extract from psyllium seed husk on GJIC in WB-src cells. The cells were treated for 48 hours with 50 µg/mL of the ethanol extract from the seed husk of psyllium. GJIC was measured using the scrape loading dye transfer technique. Bar inset=50 µm.
Figure 6C:
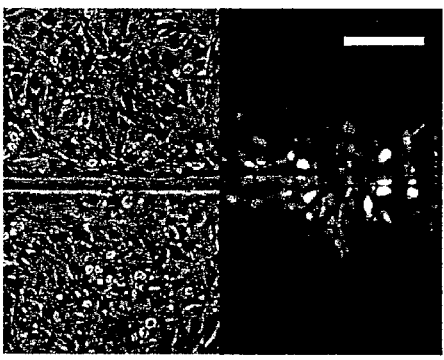
FIG. 6c shows the GJIC in WB cells transformed with neu (WB-neu cells). GJIC was measured using the scrape loading dye transfer technique. Bar inset=50 µm.
Figure 6G:
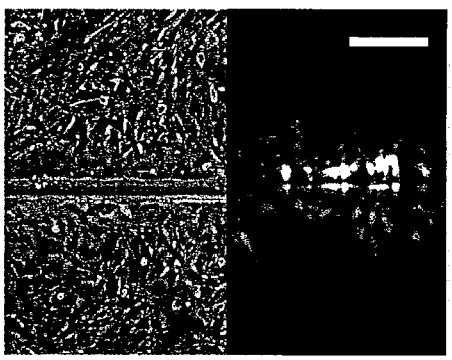
FIG. 6g shows the GJIC in WB cells transformed with myc-ras (WB-myc-ras cells). GJIC was measured using the scrape loading dye transfer technique. Bar inset=50 µm.
Figure 6D:
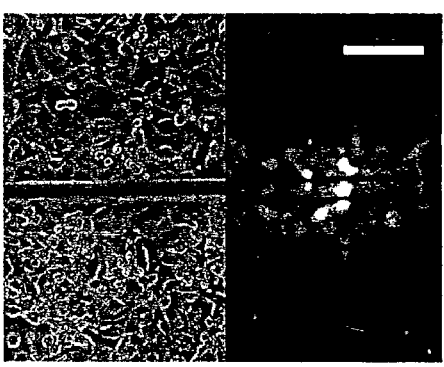
FIG. 6d shows effect of the ethanol extract from psyllium seed husk on GJIC in WB-neu cells. The cells were treated for 48 hours with 50 µg/mL of the ethanol extract from the seed husk of psyllium. GJIC was measured using the scrape loading dye transfer technique. Bar inset=50 µm.
Figure 6H:
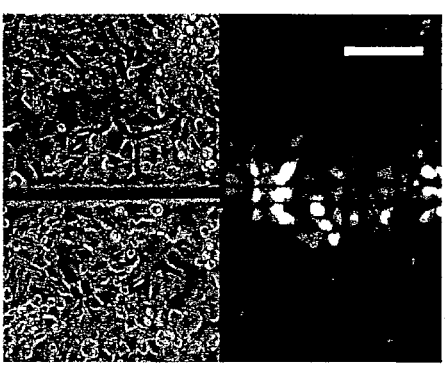
FIG. 6h shows effect of the ethanol extract from psyllium seed husk on GJIC in WB-myc-ras cells. The cells were treated for 48 hours with 50 µg/mL of the ethanol extract from the seed husk of psyllium. GJIC was measured using the scrape loading dye transfer technique. Bar inset=50 µm. A

The hypophosphorylated state of the connexins in the WB-Ha-ras cells was reversed back by 50 μg/mL of the ethanol extract of psyllium to levels similar to those of normal WB-cells, which contain both hypophosphorylated and hyperphosphorylated states of the connexins (FIG. 4). Similarly, as shown in FIGS. 5a to 5h, the ethanol extract of psyllium restored the intracellular localization of Cx43 from the cytoplasm of the untreated WB-Ha-ras cells back to the plasma membrane found in normal WB cells. Compare the intracellular location of Cx43 in the untreated WB-Ha-ras cells in FIG. 5e to its location in the cells following treatment with 25 μg/mL of ethanol extract (FIG. 5f), with 37.5 μg/mL (FIG. 5g), and with 50 μg/mL of extract (FIG. 5h) which is similar to its location in normal WB cells (FIG. 5a). The intensity and localization of immunostaining of Cx43 also showed a dose response indicating a normal intracellular pattern at a dose of 50 μg/mL and an almost normal appearance at a dose of 37.5 μg/mL. The effect of psyllium on GJIC was specific to the Ha-ras oncogene (FIG. 6a to 6h). GJIC was not restored by the ethanol extract in WB cells transfected with neu, src, and myc-ras (FIGS. 6d, 6f, and 6h, respectively).

Figure 7A:
FIG. 7a shows the largest colony formed by WB-H-ras cells in an AIG soft agar assay. One thousand cells were plated onto soft agar and overlaid with 3 mL of medium. After 3 weeks, colonies were stained and the number was counted. Photographs were taken of the largest colony found on each plate. Shown are phase contrast images (40×) of the largest colony formed in soft agar.
Figure 7C:
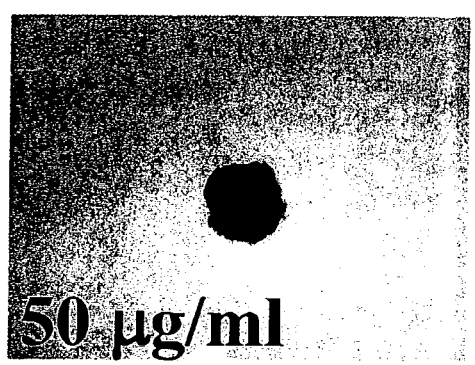
FIG. 7c shows the inhibition of anchorage independent of WB-Ha-ras cells growth by 50 µg/mL ethanol extract of psyllium seed husk after 21 days. One thousand cells were plated onto soft agar and overlaid with 3 mL of medium containing the ethanol extract. The medium was renewed with the extract every other day. After 3 weeks, colonies were stained and the number was counted. Photographs were taken of the largest colony found on each plate. Shown are phase contrast images (40×) of the largest colony formed in soft agar in response to 50 µg/ml of the extract.
Figure 7B:
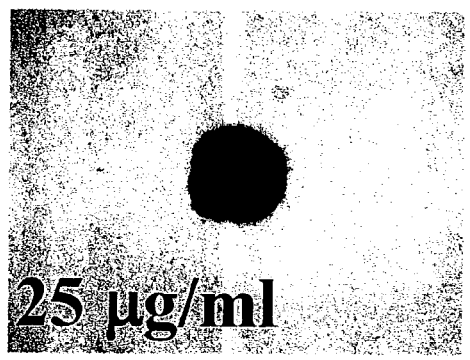
FIG. 7b shows the inhibition of anchorage independent of WB-Ha-ras cells growth by 25 µg/mL ethanol extract of psyllium seed husk after 21 days. One thousand cells were plated onto soft agar and overlaid with 3 mL of medium containing the ethanol extract. The medium was renewed with the extract every other day. After 3 weeks, colonies were stained and the number was counted. Photographs were taken of the largest colony found on each plate. Shown are phase contrast images (40×) of the largest colony formed in soft agar in response to 25 µg/ml of the extract.
Figure 7D:
FIG. 7d shows the inhibition of anchorage independent of WB-Ha-ras cells growth by 75 µg/mL ethanol extract of psyllium seed husk after 21 days. One thousand cells were plated onto soft agar and overlaid with 3 mL of medium containing the ethanol extract. The medium was renewed with the extract every other day. After 3 weeks, colonies were stained and the number was counted. Photographs were taken of the largest colony found on each plate. Shown are phase contrast images (40×) of the largest colony formed in soft agar in response to 75 µg/ml of the extract.
Figure 7E:
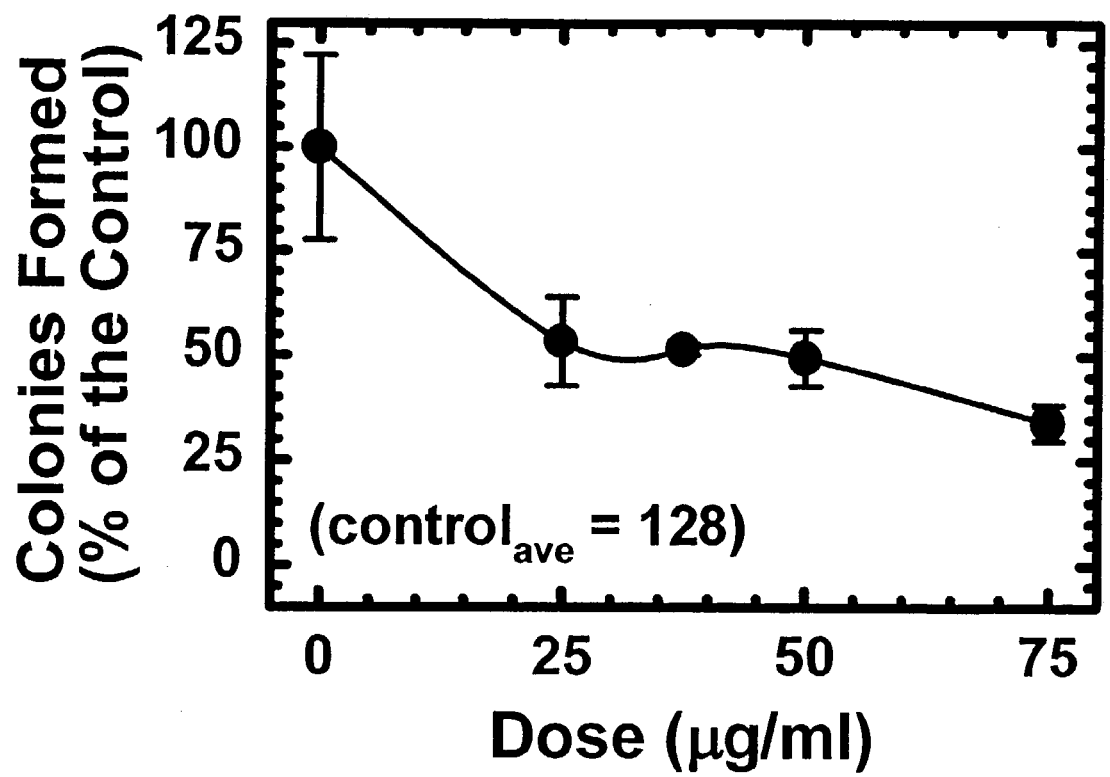
FIG. 7e shows the dose response of colony numbers in soft agar in response to psyllium for the assay shown in FIGS. 7a to 7d. Each value represents an average of colony numbers of three replicate plates±standard deviation.

The composition of the present invention inhibits anchorage independent growth (AIG). FIGS. 7a to 7d show that the ethanol extract of psyllium greatly reduced the size of the colonies formed by WB-Ha-ras cells on soft agar and that this effect increased as the doe of extract was increased from 25 μg/mL to 75 μg/mL. The photographic images shown in FIGS. 7a to 7d were representative samples of the plates. Similarly, a dose-dependent response was seen on the number of colonies formed in response to the ethanol extract of psyllium (FIG. 7e). At 75 μg/mL of extract, the number of colonies was about one quarter the number of colonies for the non-treated WB-Ha-ras cells. Normal WB cells do not form colonies on soft agar (data not shown).

Figure 8A:
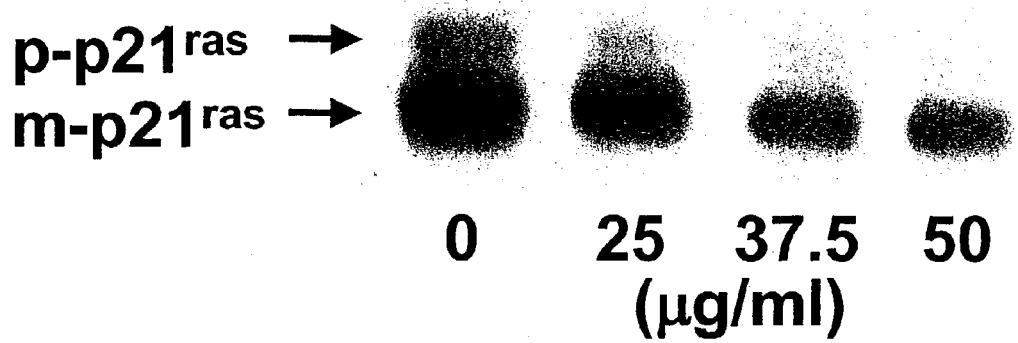
FIG. 8a shows the changes in the ras protein levels after a 48 h treatment with the EtOH extract from psyllium seed husk in WB-Ha-ras cells. The cells were treated for 48 hours with the ethanol extract from the seed husk of psyllium. Each lane was loaded with 15 µg of protein. Shown is a Western blot image of the membrane bound (m-p21$^{ras}$) and cytosolic (p-p21$^{ras}$) forms of the ras protein.
Figure 8B:
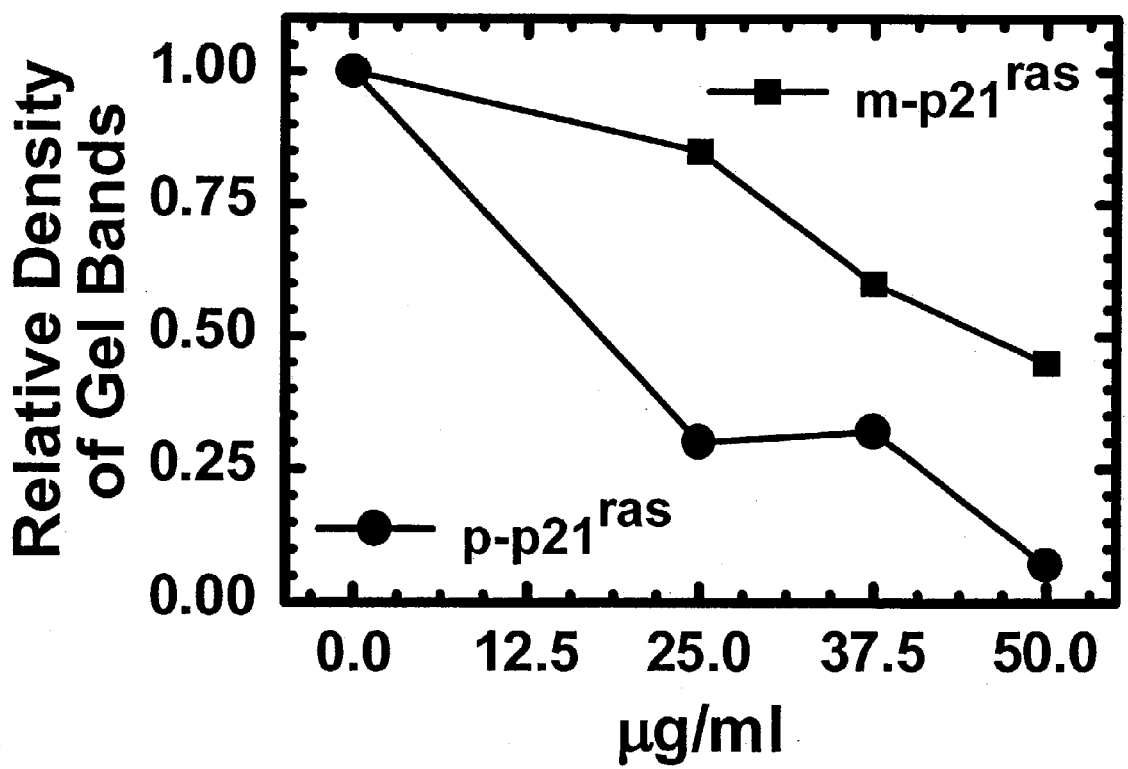
Figure 9:
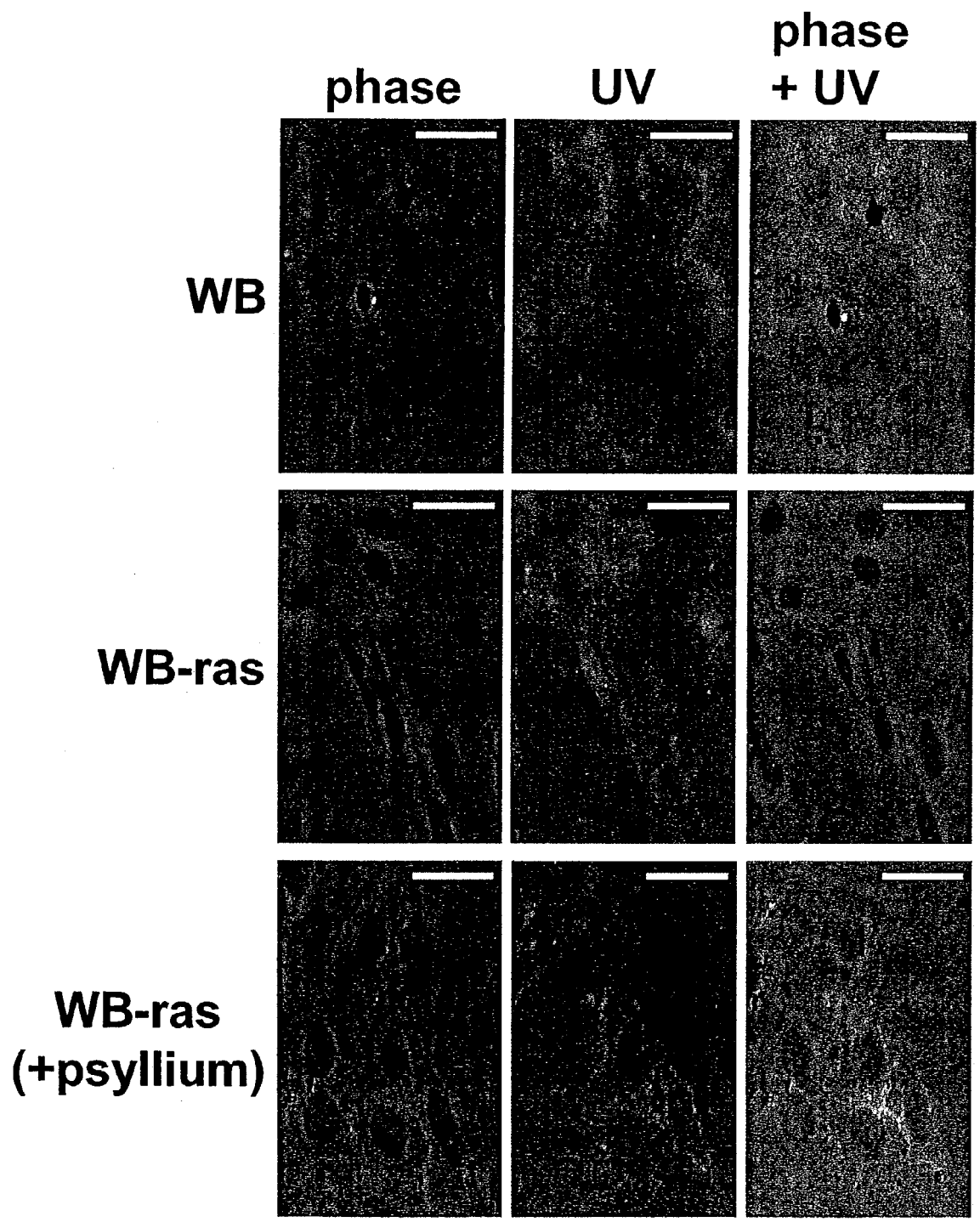
FIG. 9 shows the effect of the EtOH extract from psyllium seed husk on the intracellular localization of the ras protein in the WB-Ha-ras cells. The cells were treated for 48 hours with the ethanol extract from the seed husk of psyllium. The left panel is the phase contrast images, the middle panel is the fluorescent images of the immunostained ras protein, and the right panel is the merged images from the first two panels. Bar inset=5 µm.
Figure 10A:
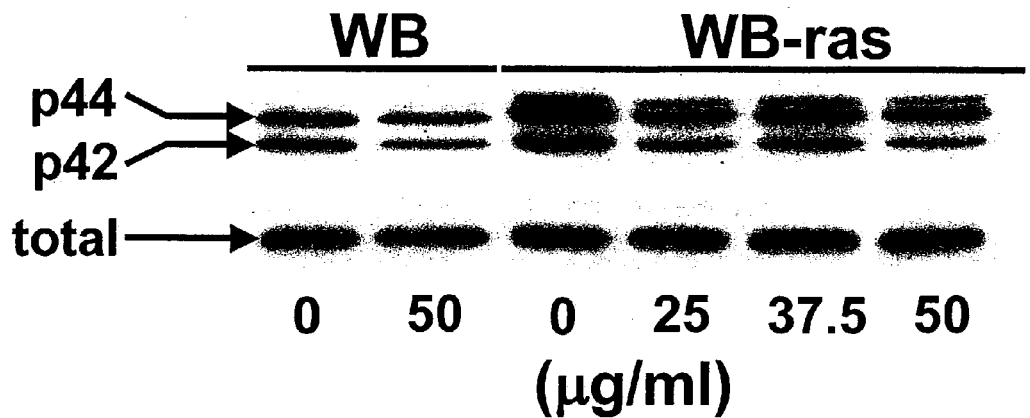
FIG. 10a shows the effect of the ethanol extract from psyllium seed husk on phospho-Erk in WB-Ha-ras cells and the normal WB-cells. The cells were treated for 48 hours with the ethanol extract from the seed husk of psyllium. Each lane was loaded with 15 µg protein. Shown is a Western blot image of Erk.
Figure 10B:
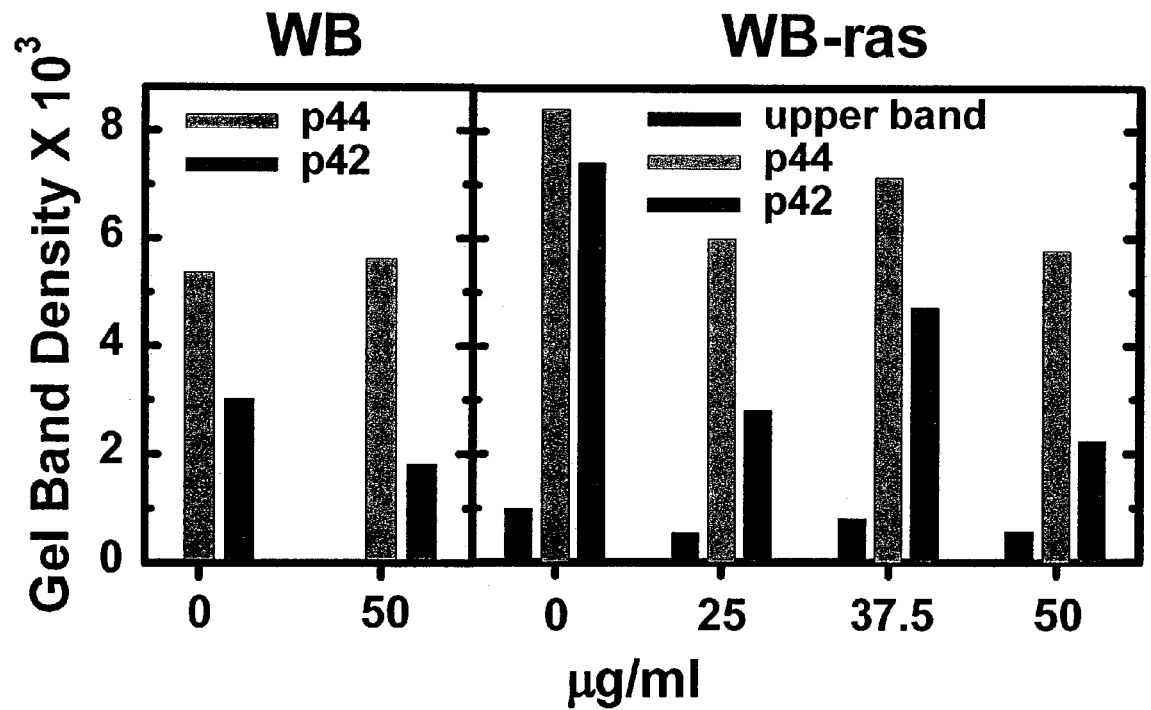
FIG. 10b shows a densiometry analysis of the Erk bands in FIG. 10a in which phospho-Erk was normalized to total Erk.

The ethanol extract of the psyllium greatly decreased the level of both the membrane (m-p21$^{ras}$) and cytosolic (p-p21$^{ras}$) forms of the ras protein at the noncytotoxic doses ranging between 0–50 μg/mL (FIGS. 8a and 8b). The intracellular-immunohistochemical localization of the ras protein in the normal WB cells was primarily on the plasma membrane in contrast to the more cytosolic localization in the ras transfected cells (FIG. 9). Treatment of WB-Ha-ras cells with the ethanol extract of psyllium resulted in shifting the immunostaining of ras protein from the cytoplasm to the plasma membrane. However, the Western blots (FIG. 8) indicated that the predominant form of the ras protein in WB-ras was the membrane form of ras (m-p21$^{ras}$). The ethanol extract of psyllium decreased the level of phosphorylation of Erk1 (p44) and Erk2 (p42) in both the normal WB and the WB-Ha-ras cells (FIGS. 10a and 10b). In addition to the p44 and p42 bands, the WB-Ha-ras also exhibited a small band above p44. The significance of this extra band was not determined, but psyllium had very little effect on this band. Although both p44 and p42 were both affected by psyllium, p42 decreased much more than the p44 band, which was at a higher level (approximately a 1:1 ratio of p44/p42) to begin with in the WB-Ha-ras cells as compared to the normal WB cells that had approximately a 1:0.5 ratio of p44:p42. The psyllium had no affect on the p44 band in the normal WB cells. The densitometry analyses were done on x-ray film exposed to the chemiluminescent bands at several times to assure that the measurement is in the linear range of the film.

The anticarcinogenic mechanism of the ethanol extract of psyllium is not known. Our results suggest that the extract of psyllium could play an important role in preventing full tumorigenic effects of the Ha-ras oncogene. The Ha-ras oncogene is known to bypass the ligand-induced activation of the extracellular receptor kinase (Erk)-mitogen activated protein kinase (MAPK) pathway (McCormick, Trends Cell Biol. 9: M53–M56 (1999)). In addition to the activation of MAPK pathways, cell proliferative events also requires the removal of a cell, such as an initiated cell, from the suppression of growth by neighboring normal cells via the blockage of gap junctional communication (Trosko and Ruch, Front. Biosci. 3: 208–236 (1998); Mehta et al., Cell 44: 187–196 (1986); Goldberg and Bertram, In Vivo. 8: 745–754 (1994)). Numerous studies have shown that transfection of normal cells with oncogenes, including ras, results in a decrease in GJIC, as well as developing tumorigenic phenotypes such as, loss of contact inhibition and AIG, high rates of cell proliferation, and induction of tumors in nude mice (Na et al., Cancer Letts. 157: 31–38 (2000); Trosko et al., Toxicol Lett. 102–103: 71–78 (1998); Jou et al., Carcinog. 16: 311–317 (1995); de-Feijter et al., Mol. Carcinog. 16: 203–212 (1996)). We showed that the extract of psyllium significantly restored GJIC in the Ha-ras transfected F344-WB rat liver epithelial cell line. This restoration of GJIC correlated with a decrease in AIG of these cells in soft agar.

Considerable evidence supports the hypothesis that inhibition of GJIC is fundamental to tumor promotion (Trosko and Ruch, Front. Biosci. 3: 208–236 (1998)), thus, suggesting that the anticarcinogenic properties of the extract of psyllium could be linked, at least in part, to effects on GJIC. A common property of tumor promoters is that they inhibit GJIC, while many anticarcinogenic compounds either block the inhibitory effects of promoters or directly restore GJIC, thereby counteracting the inhibition of GJIC by promoters (Ruch and Trosko, Drug Metab. Rev. 33: 117–121 (2001)). Structural activity relationship models demonstrated a high concordance of carcinogenic activity of compounds with their inhibitory properties of GJIC (Rosenkranz et al., Mutat. Res. 381: 171–188 (1997)). Transfection of oncogenes such as ras, neu and src but not myc into normal cells results in a reduction of GJIC of 50% or more (Jou et al., Carcinog. 16: 311–317 (1995); de-Feijter et al., Mol. Carcinog. 16: 203–212 (1996).; El-Fouly et al., Mol. Carcinog. 2: 131–135 (1989); de-Feijter et al., Mol. Carcinog. 5: 205–212 (1992)). Although myc alone does not decrease GJIC, cotransfection of myc with ras results in the complete abolition of GJIC (Hayashi et al., Cancer Lett. 128: 145–154 (1998)). When neoplastic cells come into contact with normal communicating cells, they are growth inhibited and transfection of antisense connexin into the normal cells negates the growth inhibitory effect on the neoplastic cells. A connexin 32 knockout mouse exhibited elevated rates of hepatocytes proliferation, and were more susceptible to spontaneous and initiator-induced hepatic tumor formation. A dominant-negative connexin gene completely abolishes GJIC in neoplastic cells and increases the tumorigenicity of these cells (Krutovskikh et al., Mol. Carcinog. 23: 254–261 (1998)). These published results link GJIC function with cancer.

The mechanism of how the extract of psyllium restores GJIC in Ha-ras-induced inhibition of GJIC has not been determined. Alteration in the phosphorylation patterns of connexins have been proposed as a regulatory mechanism of GJIC, however, there are several examples where altered phosphorylation of connexins did not correlate with inhibition of GJIC (Upham et al., Carcinog. 18: 37–42 (1997); Hossain et al., J. Biol. Chem. 274: 10489–10496 (1999); Hossain et al., J. Cell Physiol. 179: 87–96 (1999)). Furthermore, inhibition of GJIC by environmental contaminants does not always alter the phosphorylation status of connexins (Sai et al., Cancer Lett. 130: 9–17 (1998); Suzuki et al., Nutr. Cancer 36: 122–128 (2000); Upham et al., Int. J. Cancer 78: 491–495 (1998)). The connexins of the WB-Ha-ras cells show a hypophosphorylated protein as well as low molecular weight bands that appear under the Po band. Our results show that the extract of psyllium greatly restored the normal phosphorylation pattern of the Cx43 protein comparable to that of the normal WB cells. In normal WB cell, histochemical analysis of Cx43 results in punctate plaques on the plasma membrane, which is very low in the WB-Ha-ras cells. The extract of psyllium restored the gap junction proteins to the plasma membrane with plaques appearing the same as the normal WB cells.

At present, there is no definitive hypothesis that satisfactorily explains how growth factors and toxicants alter GJIC making it difficult to determine the mechanism of how psyllium is able to reverse the inhibitory effect of the Ha-ras oncogene, particularly since we do not know how the Ha-ras oncogene actually inhibits GJIC. However, growth factor- or ras oncogene-dependent inhibition of GJIC occurs, in part, through the MEK/Erk pathway (Warn et al., J. Biol. Chem. 273: 9188–9196 (1998); Quilliam et al., J. Biol. Chem. 274: 23850–23857 (1999)).

Curiously, our current data shows that there is a strong band that appears above the p44-band of Erk, but the identity of this band was not determined and was not greatly affected by the extract of psyllium, and its affect on the transforming properties of Ha-ras is questionable. However, the extract of psyllium did greatly decrease the p42 and p44 bands in WB-Ha-ras cells, although the p42 band was affected to a much greater extent. In the normal WB cells, only the p42 band was greatly reduced in response to the extract of psyllium. Furthermore, the WB-Ha-ras cells had unusually high levels of p42 relative to the p44 band (approximately 1:1) as compared to the normal WB cells, which had an approximate p44:p42 ratio of 0.5. These results suggest that the restoration of an approximate 2:1 ratio of p44 to p42 by the extract of psyllium might be important in restoring GJIC and inhibiting AIG in these cells.

The Western blot data showed that the total level of the ras protein decreased over 90% in the WB-Ha-ras cells as the dose of the extract of psyllium reached 50 μg/mL. Surprisingly, immunohistochemical staining showed that the intracellular localization of the ras protein was primarily in the cytoplasm in WB-ras cells and with increasing doses of the extract of psyllium, the ras protein migrated to the plasma membrane similar to that of the normal WB cells. However, densitometry analysis of Western blot data of the $p21^{ras}$ protein indicated that there was a higher membrane to cytosolic ratio of $p21^{ras}$, which is consistent with previously reported results indicating that membrane anchorage, via farnesylation, is important for the oncogenic forms of the ras-protein to transform cells (Gibbs et al., Breast Cancer Res. Treat. 38: 75–83 (1996); Agarwal et al., Mol. Carcinog. 17: 13–22 (1996)). Possibly, our antibodies were able to detect the SDS-denatured oncogenic ras protein but were unable to detect, in situ, the membrane bound Ha-ras in the cells and the extract of psyllium displaced this oncogenic form of ras allowing for the expression of the normal ras, in which the antibodies had no trouble detecting the non-denatured form of the normal ras.

The extract of psyllium had no effect on GJIC in WB-cells transfected with other oncogenes, such as neu, src, and myc. Even more interesting is the observation that the extract of psyllium had no effect on ras-myc. WB cells transfected with ras-myc exhibits a greater level of transformation as exhibited by the increase of AIG and tumor formation in nude mice, which correlates with an increased inhibition of GJIC, and represents events that occur in later progressions of a tumor (Hayashi et al., Cancer Lett. 128: 145–154 (1998)). In view of many observations that a mutated or activated ras can be detected in the early stages of carcinogenesis (Reuter et al., Blood 96: 1655–1669 (2000)), these results suggests that the extract of psyllium might be more effective at preventing the earlier stages of tumorigenesis than ameliorating the later stages, thus suggesting a chemopreventive rather than a chemotherapeutic role. This chemopreventative effect would be specific to preventing the growth effects of the mutated ras gene and not other oncogenes.

Anchorage independent growth (AIG) is a common phenotype of transformed cell lines. The underlying mechanisms leading to this phenotype in either oncogene transfected cell lines or cell lines derived from tumorigenic tissue is not completely understood but inhibition of intercellular communication through gap junctions has been determined to be one critical event in this transformation process (Ruch and Trosko, Drug Metab. Rev. 33: 117–121 (2001); Trosko and Ruch, Curr. Drug Targets 3: 465–482 (2002)). Consistent with this GJIC-dependent transformation hypothesis, the restoration of GJIC in the WB-Ha-ras cells by the extract of psyllium strongly correlated with the decrease in AIG activity of this cell line. Further, the extract of psyllium significantly decreased the size of the colonies. These results are similar to the effects of the active anti-cancer ingredient found in honeybee propolis, the phenylethyl ester of caffeic acid (CAPE), which also restored GJIC in the WB-Ha-ras cell line and inhibited AIG (Na et al., Cancer Letts. 157: 31–38 (2000)). CAPE also restored the expression of hyperphosphorylated Cx43 and decreased the protein level of $p21^{ras}$ by Western blot analysis similar to our results.

Another question that arises is whether the soluble fiber, the non-fiber, or both components are responsible for chemoprevention. Our results suggest that the extract of psyllium effect on Ha-ras in our cell line does not involve the fiber component. Which compound or compounds are involved has not been determined but a difference between two different lots from the same company suggests that the concentration of the active ingredient or ingredients can fluctuate. This indicates that identification of the active ingredient or ingredients will be critical in assessing the efficacy of various lots in restoring GJIC in cells with active oncogenic ras.

In summary, our results are consistent with the epidemiological evidence that suggests psyllium has anti-tumorigenic activity. One potential mechanism of the anti-tumorigenic activity of extracts of psyllium is its ability to restore normal GJIC in Ha-ras transformed cells, thus restoring the normal flow of cell signaling molecules between contiguous cells that are important in maintaining the homeostatic set point of growth suppression in a tissue. The implication here is that while the extract of psyllium has potential chemotherapeutic benefit, it might be restricted only to those tumors needing activated Ha-ras. Reversal of the effects of Ha-ras but not myc+Ha-ras suggests that the extract of psyllium might have a more important role in chemoprevention rather than chemotherapy. However, dietary prevention strategies will be very important, considering that advancements in the treatment of colon cancer has not changed the 5 year mortality rate at 50% for almost four decades (Wingo et al., CA-Cancer J. Clin. 45: 8–30 (1995)).

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

We claim:

1. A method for inhibiting a tumor in a patient, wherein the tumor contains cells that are incompetent for gap junctional intercellular communication (GJIC), said method comprising:
   providing to the patient a composition, in conjunction with a chemotherapy drug, comprising a mixture containing a methanol or ethanol extract of psyllium seed husk of *Plantago ovata*, which is free of fiber of the psyllium and is optionally in a pharmaceutically acceptable carrier, in an amount and for a time sufficient to inhibit the tumor in conjunction with the chemotherapy drug.

2. The method of claim 1 wherein the cells comprise a ras mutation.

3. The method of claim 1 wherein the psyllium seed husk is in the form of a powder.

4. The method of claim 1 wherein the mixture in vitro restores gap junctional intercellular communication and inhibits anchorage independent growth in mammalian cells containing a mutated ras gene and displaying unregulated proliferation.

5. The method of claim 1 wherein the patient is a human or a mammal.

6. A method for inhibiting a tumor in a patient, wherein the tumor contains cells that are incompetent for gap junctional intercellular communication (GJIC), said method comprising:
   (a) providing to the patient in conjunction with a chemotherapy drug, a non-fiber component of psyllium produced by mixing psyllium seed husk with methanol or ethanol as a solvent so as to solubiize the non-fiber component of the psyllium seed husk and separating the solvent soluble, non-fiber component from the fiber component of the psyllium to produce the non-fiber component of psyllium which is free of the fiber component; and
   (b) administering the non-fiber component of psyllium to the patient in an amount along with the chemotherapy drug for a time sufficient to inhibit the tumor.

7. The method of claim 6 wherein cells comprise a ras mutation.

8. A method of claim 6 wherein the non-fiber component is mixed with a pharmaceutically acceptable carrier.

9. The method of claim 3 wherein the psyllium seed husk is in the form of a powder.

10. The method of claim 6 wherein the non-fiber component in vitro restores gap junctional intercellular communication and inhibits anchorage independent growth in mammalian cells containing a mutated ras gene and displaying unregulated proliferation.

11. The method of claim 6 wherein the patient is a human or a mammal.

* * * * *